United States Patent [19]
Galat

[11] 3,985,792
[45] Oct. 12, 1976

[54] STABLE SODIUM ACETYLSALICYLATE AND METHOD FOR ITS MANUFACTURE

[76] Inventor: Alexander Galat, 1980 S. Ocean Drive, Hallandale, Fla. 33009

[22] Filed: Nov. 30, 1973

[21] Appl. No.: 420,381

Related U.S. Application Data

[63] Continuation-in-part of Ser. No. 211,214, Dec. 23, 1971, abandoned.

[52] U.S. Cl. .............................................. 260/480
[51] Int. Cl.$^2$ ......................................... C07C 69/14
[58] Field of Search .................................... 260/480

[56] References Cited
UNITED STATES PATENTS

| | | | |
|---|---|---|---|
| 1,217,862 | 2/1917 | Gerngross et al. | 260/480 |
| 3,064,038 | 11/1962 | Adams | 260/480 |
| 3,109,019 | 10/1963 | Schlosser | 260/480 |

OTHER PUBLICATIONS

Malkin, Chem. Abstracts, vol. 52 (1958), p. 12499.
Beilstein, vol. 10, 1st Supp. p. 29.

Primary Examiner—Jane S. Myers
Attorney, Agent, or Firm—I. Louis Wolk

[57] ABSTRACT

A novel crystalline form of sodium acetylsalicylate (sodium aspirin) is obtained by first precipitating sodium aspirin dihydrate in crystalline form and thereafter dehydrating it to form anhydrous sodium aspirin. The process is carried out under controlled conditions and the product exhibits high storage stability and other desirable physical properties.

4 Claims, No Drawings

3,985,792

STABLE SODIUM ACETYLSALICYLATE AND METHOD FOR ITS MANUFACTURE

RELATED APPLICATIONS

This application is a continuation-in-part of copending application, Ser. No. 211,214, filed Dec. 23, 1971, now abandoned.

SUMMARY OF THE INVENTION

In accordance with the invention a highly concentrated aqueous solution of sodium aspirin is formed, the concentrated solution is then contacted with a water miscible organic solvent, preferably one selected from among the $C_3$ and $C_4$ aliphatic alcohols, added gradually at temperatures between ordinary room temperature and the freezing point of needle-like crystals is avoided. The sodium aspirin dihydrate crystallizes out in the form of granular plate-like crystals which are then isolated and dehydrated to form pure anhydrous sodium aspirin in the form of stable granular free-flowing crystals also having a plate-like structure.

DETAILED DESCRIPTION OF THE INVENTION

Ever since the discovery of the valuable analgesic and antipyretic properties of acetylsalicylic acid (aspirin) some 60 years ago, continuous attempts have been made to prepare a stable, neutral, water soluble derivative of this compound. Such a derivative would offer a number of important advantages over aspirin itself — it could be given in solution form to patients unable to swallow tablets, it would be more readily absorbed, and, most important, it would reduce the incidence of gastrointestinal disorders resulting from the acidic nature and the low water solubility (1 g/100 ml.) of aspirin.

In attempts to prepare a stable, neutral, water soluble derivative of aspirin, a very large number of salts and other derivatives of this compound have been synthesized: lithium, ammonium, sodium, potassium, calcium and magnesium salts, amine and amino acid salts, calcium salt complexes with urea, with amino acids and the like. Unfortunately, these compounds proved to be of unreliable stability on storage. Apparently, neutralization of the carboxyl group of acetylsalicylic acid makes the acetyl group extraordinarily sensitive to hydrolysis and other types of decompositon, and, as a result, many of these compounds rapidly decompose on storage with the formation of various breakdown products such as salicylic acid, acetic acid and others.

Especially troublesome is the fact that the storage behavior of these aspirin salts and other derivatives is extremely erratic and unpredictable. Different lots of such compounds, prepared by the same process, vary greatly in stability; some lots decomposing after several weeks storage, others after several months, while still others remain in apparently good condition for even longer periods only to begin to decompose suddenly and at a very rapid rate for no apparent reason. This unpredictable behavior undoubtedly explains in large measure the contradictory claims regarding the stability of salts and various other derivatives of aspirin made by various ingestigators in the past.

Simple salts of aspirin are much more soluble, are more potent and longer lasting pharmacologically, less irritating to the stomach, and more palatable than aspirin itself. Of such salts sodium acetylsalicylate (sodium aspirin) is the most advantageous with respect to solubility, speed of action, serum levels and palatability. Sodium aspirin is almost 1000 times as soluble in water as aspirin itself. It is a neutral, well tolerated compound, readily absorbed from the gastrointestinal tract. It is faster acting and more predictable in its action than aspirin itself and its various formulations. Sodium aspirin is a compound with a salty, but acceptable taste, when taken in solid form, as is nearly tasteless when taken in solution. Unfortunately, as is true with many other salts of aspirin (potassium, ammonium, lithium, calcium, magnesium, etc. salts), the sodium aspirin of the prior art is obtained as an unstable compound which decomposes appreciably even after only several months storage at room temperature. The absence of a practical and commercially feasible process for the manufacture of a stable sodium aspirin has prevented the use of this valuable drug in medical practice.

Sodium aspirin has been prepared by a variety of methods. Thus, aspirin has been reacted with sodium carbonate in the presence of small amounts of organic solvents, such as methanol, methyl and ethyl formate, methyl and ethyl acetate, and the like. The resulting product is very impure and unstable, probably due to the heterogeneous nature of the reaction in which insoluble reactants are converted into an insoluble reaction product. Sodium aspirin prepared by this method fuses after storage for several months with production of considerable amounts of acetic and salicylic acids.

Sodium aspirin has also been prepared by reacting aspirin with compounds such as sodium bicarbonate, sodium silicate, etc. in aqueous solution. While the reaction is homogeneous, the product cannot be directly isolated from the reaction mixture because of its great solubility in water. Consequently, removal of water by distillation is required. However, not only are such distillations expensive and time consuming on a commercial scale, but the sodium aspirin undergoes hydrolysis during the distillation resulting in low yields of an impure product or of poor stability. In order to minimize hydrolytic decomposition during the distillation operation, it has been proposed that the removal of water be conducted at very low temperatures and pressures while maintaining the reaction mixture in the frozen state. This is obviously an expensive, tedious and impractical process, unsuitable for the production of a low cost product such as an aspirin derivative. Moreover, this process also produces a product of unsatisfactory stability.

In order to avoid the distillation operation, it has been proposed to react aspirin with sodium bicarbonate in the presence of an extremely small amount of water, just sufficient to wet the mixture. However, again, probably because of the heterogeneous nature of the reaction the product obtained is unstable and impure, being contaminated with unreacted aspirin and sodium bicarbonate.

The objects of this invention are accomplished by preparing a highly concentrated aqueous solution of sodium aspirin, treating this solution under such conditions as to cause the sodium aspirin to crystallize in the form of a hydrate, isolating the hydrate and then dehydrating the hydrate to produce anhydrous sodium aspirin in the form of a stable, free flowing and non-caking particulate solid. Unexpectedly, this product is obtained in the form of plate-like granular crystals rather than the elongated needle-like crystals of the prior art.

When a water miscible organic solvent such as a lower aliphatic alcohol, is added to an aqueous solution of sodium aspirin in accordance with the usual and conventional procedures of organic chemistry, a precipitate of sodium aspirin in the form of needle-like crystals is obtained. A typical procedure of this kind is described in Example I.

EXAMPLE I

A solution of sodium aspirin obtained by reacting 100 g. of aspirin with sodium bicarbonate in the presence of 50 ml. water was mixed with 1,000 ml. of isopropanol at 5° C. The resulting mixture was refrigerated for 5 hours, the crystalline product filtered, washed with cold isopropanol, then washed with benzene and dried at room temperature. The yield was 40 g. (35.7% theory).

The product was in the form of voluminous white needles melting at about 220° C. The purity of the product was 99.5% ± 0.2%. The analysis as well as the melting point correspond to the anhydrous sodium salt of acetylsalicylic acid. The anhydrous sodium aspirin obtained exhibits all the characteristics of sodium aspirins produced by various methods of the prior art, including instability.

I have discovered that sodium aspirin possessing high storage stability as well as other desirable characteristics (such as free-flow and non-caking characteristics and ready compressibility) is obtained when this salt is crystallized first in hydrated form and then dehydrated. This is all the more surprising since the intermediate hydrate is an unstable compound which readily breaks down into acetic acid, salicylic acid and other decomposition products, exhibiting substantial decomposition with 24 hours at room temperature (several per cent).

When a lower aliphatic alcohol such as isopropanol is added to a concentrated solution of sodium aspirin without any special precautions, there is produced, as described in Example I above, a voluminous precipitate of anhydrous sodium aspirin in the form of needle-like crystals. However, when the same operation is performed in accordance with the special conditions and procedures described by way of illustration in detail in Example II, post, there is formed a hydrated sodium aspirin which in contrast to the needle-like crystals of Example I, is obtained in the form of granular, free-flowing crystals. I have further discovered that the latter product, upon dehydration, produces an anhydrous sodium aspirin differing in its crystalline form and other properties from the anhydrous form obtained directly. This new anhydrous form of sodium aspirin of my invention is a free-flowing solid, in the form of granular plate-like crystals or platelets, exhibiting good stability on storage and is readily compressible into tablets and other dosage forms.

In the operation of my process, I prefer to use as a solvent, a $C_3$ or $C_4$ aliphatic alcohol such as propanol, isopropanol, butyl alcohol, isobutyl alcohol, or tertiary butyl alcohol, or mixtures of any of these. Generally, isopropanol is a useful, inexpensive and preferred solvent. The solvent may readily be recovered for re-use by distillation.

I have further discovered that the yield of sodium aspirin is very substantially increased when the process of my invention is used over that obtained when the anhydrous form is produced directly as described in Example I.

The method used for the preparation of the concentrated aqueous solution of sodium aspirin employed as a starting material in the practice of my invention is immaterial. Aqueous solutions of sodium aspirin may be prepared by treating aspirin with neutralizing agents such as sodium hydroxide, sodium carbonate and sodium bicarbonate. Due to the high alkalinity of the first two agents and resulting extensive hydrolysis, sodium bicarbonate is the preferred neutralizing agent.

EXAMPLE II

A solution of sodium aspirin obtained by reacting 100 g. aspirin with sodium bicarbonate in the presence of 50 ml. water was cooled to 5° C and 1,000 ml. of isopropanol added slowly with stirring and cooling. The rate of addition of the alcohol was about 300 ml. per hour, the rate of stirring about 60 RPM, and the temperature was maintained at 5° C. The resulting crystalline precipitate was separated by filtration, washed with cold isopropanol followed by benzene, and then dried at room temperature. Yield: 103 g. (78% theory).

The purity of the product was 99.5% ± 0.2% and it was obtained in the form of heavy granular, free-flowing crystals. Analysis showed that the product contained 15% water of crystallization, corresponding to sodium aspirin dihydrate.

EXAMPLE III

The procedure of Example II was carried out except that 1,000 ml. of tertiary butyl alcohol was added slowly with stirring and cooling to maintain a temperature of about 5° C. The resulting granular, plate-like dihydrate crystalline precipitate was separated, washed with cold tertiary butyl alcohol, followed by benzene and dried at room temperature. The yield was 99 gms. (75% theory).

The melting of the dihydrate was characterized by the following behavior. As the temperature of the dihydrate was raised rapidly, the compound shrank over the temperature range 20° C, to about 105° C., and gradually became wet. It melted at about 125° C then resolidified in the range of 140°–150° C, there being no further apparent change from 150° to 250° C.

The dihydrate is somewhat unstable and undergoes substantial decomposition into salicylic acid, acetic acid and other compounds on standing for more than a few hours at room temperature, and decomposes even more rapidly at higher temperatures. For this reason, it is advisable to promptly separate the hydrate and carry out the dehydration to the anhydrous form.

The above Examples show that the anhydrous acicular form and hydrated sodium aspirin are formed under closely similar conditions; only a slight variation in the operating conditions will produce either the anhydrous compound or the dihydrate. It is helpful although not absolutely necessary, to seed the reaction mixture with a crystal of the hydrated salt when the latter form is desired.

To produce the hydrated form of sodium aspirin, particularly to secure this product in high yield, careful control must be exercised over operating variables. In the first place, the aqueous solution of sodium aspirin employed as the starting material must be highly concentrated so the liquid portion of the reaction mixture obtained at the conclusion of the operations described in Examples II and III has a very low content of free water. If this precaution is not observed, the recovery of hydrated sodium aspirin is very materially reduced due to the solubility thereof in solvent containing appreciable amounts of water. On the other hand, the initial aqueous sodium aspirin solution obviously must provide sufficient water to form the dihydrate of the sodium aspirin it contains during the course of the subsequent operations. As will be seen, the aqueous sodium aspirin solution of Examples II and III contains about 2.5 times the stoichiometric requirement of water for the dihydrate forming reaction, thus, providing more than sufficient water for completion of this reaction, but at the same time resulting in a final reaction mixture containing appreciably less than 5% free water.

Also, to secure sodium aspirin in hydrated form, it is advantageous to maintain other operating variables essentially as described in Example II when operating on a similar scale.

The concentration of the aqueous sodium aspirin starting solution employed, the amount of isopropanol employed, the rate of addition of this alcohol, the temperature maintained during the addition of isopropanol or other solvent, and the rate of stirring, all as set forth in Example II, have been found be experiment to be an advantageous combination of operating variables from a practical standpoint.

These amounts and conditions while preferred however, are not critical for the successful practice of my invention. Thus, lowering the temperature of isopropanol or other solvent, addition to $-15°$ C., does not substantially increase the yield of hydrated sodium aspirin. It has also been found that increasing the amount of isopropanol to more than 10 parts per part of aspirin also does not substantially affect the yield, whereas a significant drop in yield is observed when this ratio is lowered materially below 5 parts by weight for each part by weight of aspirin.

In general however, the best results obtained is by utilizing a concentrated sodium aspirin solution containing about 1 to 2.5 parts of sodium aspirin by weight for each part by weight of water, with a preferred concentration of 0.4 to 0.6 parts of water for each part of sodium aspirin. Precipitation of sodium aspirin dihydrate is generally obtained using at least several parts of solvent by weight for each part by weight of sodium aspirin within the range of about 5–10 parts of solvent for each part of sodium aspirin, with greater excess not contributing greatly to the process, but undesirable only from the standpoint of economics of recovery. The temperature at which precipitation may be carried out will range from the freezing point of the solution to room temperature, and preferably, between about $-10°$ C and $+10°$ C.

Within certain limits, the rate of addition of solvent as well as the rate of stirring shown in Example II are also not critical. It is to be noted however, that rate of addition of isopropanol and rate of agitation are closely inter-related. Thus, at a given rate of agitation the addition of isopropanol must be so adjusted as to prevent formation of the acicular anhydrous salt. Formation of this anhydrous salt is readily detected by direct visual examination of a sample of the mixture. The presence of needle-like crystals indicates production of anhydrous salt, thus requiring for the selected rate of agitation a slower rate of addition of the alcohol. As will be obvious to those skilled in the art, the relative rates of addition and stirring will vary, depending upon the size of the batch, type of equipment used, and mechanical factors involved. Thus, these factors can be predetermined or controlled during production so as to avoid formation of the needle-like crystals.

Additionally, rate of stirring exhibits another quite independent effect. Rate of stirring has a direct effect on the size of the crystals formed; the slower the rate of stirring, the larger the crystals, and vice-versa. It is often desirable that crystals of a certain size be prepared since this factor affects flow characteristics of the dehydrated product as well as its suitability and convenience in the preparation of dosage forms such as tablets.

The previous Examples show that although the quantities of the reactants are identical in both, the yield is more than twice as high when the product is precipitated in the form of the hydrate followed by dehydration, than when the anhydrous form is produced directly, undoubtedly due to the lesser solubility of the hydrate in the final reaction medium.

The sodium aspirin dihydrate of this invention may be readily converted to anhydrous sodium aspirin by removing the water of hydration by heating in vacuum at moderate temperatures, such as in the range of $20°-50°$ C. There is thus obtained from 100 g. of the hydrate, about 85 g. of pure anhydrous salt, melting at about $220°$ C.

It is possible to convert needle-like anhydrous crystals of sodium aspirin of the prior art to the new granular form of anhydrous sodium aspirin of this invention by first hydrating the needle-like anhydrous crystals followed by dehydration. This procedure is illustrated in the following Example.

EXAMPLE IV 100 g. of anhydrous sodium aspirin of the needle-like crystalline form were dissolved in 50 ml. water, cooled to $5°$ C, and then treated with isopropanol exactly as described in Example II. After filtration of the crystalline precipitate which was the dihydrate, washing, and dehydration to remove water of hydration, there was obtained about 75 g. of a product possessing the granular anhydrous crystalline form of the sodium aspirin of this invention. The purity of the product was $99.5\% \pm 0.2\%$.

The anhydrous salt of this invention differs in several important respects from the anhydrous salts prepared by prior art procedures or the product described in Example I. The great different in gross physical appearance between the anhydrous sodium aspirin of this invention and the sodium aspirin prepared in accordance with Example I is apparent on visual examination due to the difference in appearance between plate-like and needle-like crystals.

Of greatest practical importance is the fact that the stability of the product of this invention is sufficiently high for all practical purposes. Kept at room temperature, in a closed vial for one year, the extent of the decomposition is uniformly less than 3.5%.

The anhydrous sodium aspirin of this invention is a free-flowing, non-caking, granular mass of plate-like crystalline habit. These free-flowing, non-caking granular platelets are directly and easily compressible into pharmaceutical tablets and similar unitary dosage forms exhibiting good stability on storage. This had not been found to be true in the case of the needle-like crystals of the prior art, which require preliminary grinding and compacting before compression which leads to contamination and loss of stability.

I claim:

1. A process for the production of anhydrous sodium aspirin in the form of plate-like crystals which comprises forming a concentrated aqueous solution of sodium aspirin containing about 1 to 2.5 parts by weight of sodium aspirin for each part by weight of water, gradually and thoroughly admixing with said solution a water miscible organic solvent selected from the 3 and 4-carbon saturated aliphatic alcohols and mixtures thereof in the proportion of about 5 to 10 parts by weight of solvent for each part by weight of sodium aspirin as the sole precipitating agent to precipitate hydrated plate-like crystals of sodium aspirin dihydrate while maintaining the temperature during precipitation between about −10° C and +10° C, separating said dihydrate, and removing the water of hydration to obtain substantially pure anhydrous sodium aspirin.

2. A process according to claim 1 wherein the solvent is isopropyl alcohol.

3. A process according to claim 1 wherein the sodium aspirin is dissolved in 0.4 to 0.6 parts by weight of water, wherein the solvent is isopropanol and wherein said solvent is added in the proportion of at least 5 parts by weight for each part by weight of sodium aspirin.

4. Pure stable anhydrous sodium aspirin in the form of plate-like crystals produced by precipitation of plate-like crystals of sodium aspirin dihydrate from a concentrated aqueous solution of sodium aspirin containing about 1 to 2.5 parts by weight of sodium aspirin for each part by weight of water by the gradual and thorough admixing therewith of a water miscible organic solvent selected from the 3 and 4-carbon saturated aliphatic alcohols and mixtures thereof in the proportion of about 5 to 10 parts by weight for each part by weight of sodium aspirin while maintaining the temperature during precipitation, between about −10° C to +10° C, followed by separation of precipitated plate-like crystals of sodium aspirin dihydrate and removal of water of hydration therefrom.

* * * * *